(12) United States Patent
Popp et al.

(10) Patent No.: US 8,927,752 B2
(45) Date of Patent: Jan. 6, 2015

(54) SEPARATING CYCLIC SILOXANES FROM SHORT-CHAIN SILOXANES HAVING TERMINAL HYDROXYL GROUPS

(75) Inventors: Alfred Popp, Unterhaching (DE); Christine Kaes, Burghausen (DE); Klaus Kaeppler, Burghausen (DE); Ulrike Buettner, Bobersen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/233,070

(22) PCT Filed: Jul. 11, 2012

(86) PCT No.: PCT/EP2012/063573
§ 371 (c)(1),
(2), (4) Date: Jan. 15, 2014

(87) PCT Pub. No.: WO2013/013980
PCT Pub. Date: Jan. 31, 2013

(65) Prior Publication Data
US 2014/0155644 A1  Jun. 5, 2014

(30) Foreign Application Priority Data
Jul. 25, 2011  (DE) .......................... 10 2011 079 751

(51) Int. Cl.
*C07F 7/20* (2006.01)
*C07F 7/21* (2006.01)
*C08G 77/16* (2006.01)
*C08G 77/34* (2006.01)

(52) U.S. Cl.
CPC . *C07F 7/21* (2013.01); *C08G 77/16* (2013.01); *C08G 77/34* (2013.01)

USPC .......................................... 556/463; 556/460

(58) Field of Classification Search
CPC ............... C07F 7/20; C07F 7/089; C07F 7/21
USPC ....................... 556/460, 463; 528/10; 510/115
See application file for complete search history.

(56) References Cited

U.S. PATENT DOCUMENTS

| 3,493,595 A | 2/1970 | Strasser et al. |
| 4,096,160 A | 6/1978 | Ashby |
| 4,113,760 A | 9/1978 | Frey et al. |
| 2002/0161158 A1* | 10/2002 | Burkhart et al. ................ 528/10 |

FOREIGN PATENT DOCUMENTS

| DE | 26 30 744 A1 | 2/1978 |
| DE | 19507594 A1 | 9/1996 |
| EP | 0543665 A1 | 5/1993 |
| EP | 1013698 A1 | 6/2000 |
| WO | 9410228 A1 | 5/1994 |

OTHER PUBLICATIONS www. engineeringtoolbox.com/saturated-steam-properties-d_457. html, published Feb. 22, 2006.*

* cited by examiner

*Primary Examiner* — Sudhakar Katakam
*Assistant Examiner* — Pancham Bakshi
(74) *Attorney, Agent, or Firm* — Brooks Kushman P.C.

(57) ABSTRACT

Cyclic siloxanes are separated from short chain hydroxyl-terminated siloxanes by contact with steam at at least 650 hPa absolute. The cyclic siloxanes and other components which are separated by use of steam can be recovered by phase separation, and preferably used in other processes.

9 Claims, No Drawings

SEPARATING CYCLIC SILOXANES FROM SHORT-CHAIN SILOXANES HAVING TERMINAL HYDROXYL GROUPS

CROSS-REFERENCE TO RELATED APPLICATIONS

This application is the U.S. National Phase of PCT Appln. No. PCT/EP2012/063573 filed Jul. 11, 2012, which claims priority to German application DE 10 2011 079 751.3 filed Jul. 25, 2011, the disclosures of which are incorporated in their entirety by reference herein.

BACKGROUND OF THE INVENTION

1. Field of the Invention

The invention relates to a method for separating cyclic siloxanes from short-chain siloxanes having terminal hydroxyl groups and to short-chain siloxane having a low content of cyclic siloxanes.

2. Description of the Related Art

Siloxanes having terminal hydroxyl groups, for example polydimethyl siloxanes having terminal hydroxyl groups, polydimethyl(methylvinyl)siloxanes having terminal hydroxyl groups and polydimethyl(methylphenyl)siloxanes having terminal hydroxyl groups are used as crosslinking agents, plasticizers and intermediates in the silicone industry. These siloxanes are produced, for example, by hydrolysis of dimethyldichlorosilane, methylvinyldichlorosilane or methylphenyldichlorosilane in the presence of chlorosiloxanes or of alkoxysilanes. The resultant product is separated from water in order to prepare a hydrolyzate mixture which, in addition to the desired short-chain siloxanes having terminal hydroxyl groups, also contains cyclic siloxanes.

The cyclic siloxanes D4 (octamethylcyclotetrasiloxane), D5 (decamethylcyclopentasiloxane) and D6 (dodecamethylcyclohexasiloxane) are listed by the OECD as "high production volume chemicals" (>1000 t/year in at least one OECD member). Owing to the great production volume thereof and the increasing use which results in an increased exposure of humans and increased introduction into the environment, siloxanes have been studied with respect to ecotoxicological criteria such as environmental persistence and bioaccumulation, and also with respect to toxic effects thereof to humans and animals. Siloxanes fulfill some of the preconditions necessary for classification as PBT substances ("persistence, bioaccumulation, toxicity"). They are relatively stable, can be transported over wide distances in the atmosphere and have a sufficient physical and biological half life in order to accumulate in the environment and in aquatic creatures.

From this aspect there is a need to provide short-chain siloxanes having terminal hydroxyl groups having a low content of cyclic siloxanes, and a method for production thereof.

Methods for producing linear siloxanes and separating them from volatile compounds, inter alia from cyclic siloxanes, are known (see methods A-D).

(Method A)

WO 9410228 describes a method for purifying liquid polysiloxane which contains impurities as a low-molecular-weight fraction by vaporizing the low-molecular-weight fraction. Here, owing to the low boiling point, the low-molecular-weight fractions of the short-chain siloxane are also separated conjointly (see in this context the present comparative example) and the chain length distribution of a short-chain siloxane having terminal hydroxyl groups is changed. The consequence thereof is a changed property profile such as, for example, a higher viscosity, etc., or differences in the application properties, e.g. as plasticizer.

(Method B)

U.S. Pat. No. 4,096,160 describes separating low-boiling cyclic polysiloxanes from linear hydroxyl-terminal diorganopolysiloxane liquid using steam under a partial vacuum of at most 70 mm Hg. In this process, residual cyclene contents in the linear hydroxyl-terminal diorganopolysiloxane of <2% are achieved. However, on account of the low boiling point, the low-molecular-weight fractions of the short-chain siloxane are also separated conjointly and the chain-length distribution of the desired short-chain siloxane having terminal hydroxyl groups is changed thereby.

(Method C)

EP 1013698 describes a method for the continuous reduction of the amount of cyclic organosiloxanes in a circulated process stream in which a low-boiling fraction containing low-molecular-weight cyclic organosiloxanes and an inert solvent is separated from the process stream by distillation. In this process, as in method A, the low-molecular-weight fractions of a short-chain siloxane are also separated conjointly.

(Method D)

EP 543665 claims a purification method for long-chain siloxanes by contacting the siloxane with steam and distilling out and separating the impurities with the steam. The impurities comprise cyclic and short-chain siloxanes.

SUMMARY OF THE INVENTION

The invention relates to a method for removing cyclic siloxanes from a mixture which contains cyclic siloxanes and short-chain siloxanes having terminal hydroxyl groups, wherein the cyclic siloxanes are separated using a steam stream at at least 650 hPa absolute.

Surprisingly, it has been found that short-chain low-cyclene siloxanes having terminal hydroxyl groups are obtained when steam is contacted with siloxane contaminated by cyclic siloxanes, since the short-chain siloxanes having terminal hydroxyl groups are not separated by the steam.

DETAILED DESCRIPTION OF THE PREFERRED EMBODIMENTS

The cyclic siloxanes have, in particular, the general formula (I)

$$(R^1R^2SiO)_m \qquad (I),$$

where $R^1$ are alkyl groups having 1 to 12 carbon atoms, $R^2$ have the meanings of $R^1$, aryl groups having 5 to 30 carbon atoms, or alkenyl groups having 2 to 12 carbon atoms, and is an integer from 3 to 20.

The substituent $R^1$ preferably has 1 to 12 carbon atoms and can be, for example, methyl, ethyl, propyl, tert-butyl and hexyl. Most preferably, each $R^1$ substituent is methyl. The substituent $R^2$ preferably has at most 10 carbon atoms and can be, for example, methyl, ethyl, propyl, tert-butyl, hexyl, phenyl, tolyl, xylyl, naphthyl and vinyl. Preferably, each $R^2$ independently of one another is selected from methyl and vinyl. Most preferably, $R^2$ is selected from methyl and vinyl and each $R^2$ is the same, that is to say all $R^2$ are either methyl or vinyl. The value of m is preferably 4 to 10.

The short-chain siloxanes having terminal hydroxyl groups have, in particular, the general formula (II)

$$HO(R^3R^4SiO)_nH \quad (II)$$

where
R³ are alkyl groups having 1 to 12 carbon atoms,
R⁴ has the meanings of R³, aryl groups having 5 to 30 carbon atoms, or alkenyl groups having 2 to 12 carbon atoms, and is an integer from 2 to 100.

Examples of R³ and preferred meanings of R³ are listed hereinbefore for R¹. Examples of R⁴ and preferred meanings of R⁴ are listed hereinbefore for R². Preferred values for n are 3 to 50, in particular at most 25.

Mixtures which contain cyclic siloxanes and short-chain siloxanes having terminal hydroxyl groups can be produced by methods known to those skilled in the art. For example, these mixtures can be produced by direct hydrolysis of one or more substituted dichlorosilanes which can subsequently optionally be further modified by equilibration.

The cyclic siloxanes which have similar properties with respect to the boiling point to the short-chain siloxanes having terminal hydroxyl groups are removed from the mixture by contacting with steam, without the chain-length distribution of the short-chain linear siloxane being substantially affected, or individual components of the short-chain siloxane being removed.

In this process, the fraction of the cyclic siloxanes in the mixture with the short-chain siloxanes having terminal hydroxyl groups before use of the method according to the invention, based on the sum of D4+D5+D6 (corresponds to m=4 to 6) is in a range of 4%-25%, preferably in a range of 5%-20%, and most preferably in a range of 5%-15%.

Preferably, in this case, $R^1=R^2=$methyl group in the general formula I.

The fraction of the cyclic siloxanes in the mixture with the short-chain siloxanes having terminal hydroxyl groups after use of the method according to the invention, based on the sum of cyclic siloxanes of the general formula (I) where m=4 to 6 is in a range of 0-20,000 ppm by weight, preferably in a range of 0-15,000 ppm by weight, and most preferably in a range of 0-10,000 ppm by weight.

Preferably, in this case, $R^1=R^2=$methyl group in the general formula I.

The invention also relates to short-chain siloxanes of the general formula (II) which have at most a content of cyclic siloxanes of the general formula (I) where m=4 and m=5 of, in each case, at most 0.5% by weight, in particular at most 0.2% by weight, and where m=6 of at most 1% by weight, in particular at most 0.5% by weight. These low-cyclene siloxanes can be obtained by the method hereinbefore.

Preferably in this case, $R^1=R^2=$methyl group in the general formula I. Preferably, in this case, $R^3=R^4=$methyl group in the general formula II. Equally preferably, $R^3=$methyl group and $R^4=$methyl group or vinyl group.

The siloxane mixture can be contacted with steam in any manner known to those skilled in the art, for example by steam distillation. The method can be carried out continuously or batchwise, preferably continuously.

In order to prevent short-chain siloxanes having terminal hydroxyl groups being passed over together with the steam, the method is carried out at pressures of at least 650 hPa. Preferably, the method pressure is 800 hPa to 5000 hPa absolute. Most preferably, the method pressure is 900 hPa to 2000 hPa absolute.

The method is carried out at temperatures greater than or equal to the temperature of the steam used. Preferably, the temperature is from 100 to 200° C. Most preferably, the temperature is from 100 to 150° C.

The separated mixture of steam and cyclic siloxanes is precipitated by methods known to those skilled in the art, for example by condensation in a cooler. The cyclic siloxanes, which are relatively poorly water-soluble at temperatures lower than the process temperature are then preferably separated by physical separation operations (phase separation) from the condensed steam and can optionally be reused in processes, for example processes similar to the method described in DE 2630744 A.

All symbols hereinbefore of the formulae hereinbefore have their meanings in each case independently of one another. In all of the formulae, the silicon atom is tetravalent.

In the examples hereinafter, if not stated otherwise in each case, all amounts and percentages are based on the weight, all pressures are 1000 hPa (absolute) and all temperatures 20° C.

EXAMPLE

A 2 l flask is approximately ⅔ filled with water which is heated to boiling. The resultant steam is passed into a 500 ml flask which is filled with 230 g of a mixture of the composition listed in table 1 as starting mixture that is brought to and maintained at 100° C., in such a manner that the point of introduction is below the liquid surface.

The temperature in the 500 ml flask is controlled in such a manner that as little water as possible condenses there (temperature always >100° C.). The steam passed through the mixture is condensed in an ascending cooler and the condensate is collected in a further flask. Steam is passed through the mixture until the effluent of the cooler condensate no longer exhibits phase separation.

The aqueous phase is separated both in the flask having the starting mixture and in the flask having the condensate.

After the treatment, 198 g of the composition listed in table 2 remain of the starting mixture.

From the vapor condensate, 23 g of a siloxane mixture of the composition listed in table 3 precipitate out.

TABLE 1

| | | Composition of the starting mixture | | | |
|---|---|---|---|---|---|
| Hexamethyl-cyclotri-siloxane | Octamethyl-cyclotetra-siloxane | Decamethyl-cyclopenta-siloxane | Dodecamethyl-cyclohexa-siloxane | Tetradecamethyl-cyclohepta-siloxane | Polysiloxane of the formula II having $R^1 = R^2 = CH_3$ and a mean chain length of n = 12 |
| 0.1% | 1.3% | 6.5% | 2.3% | 0.5% | 89.3% |

TABLE 2

Composition after use of the method

| Hexamethyl-cyclotri-siloxane [D3] | Octamethyl-cyclotetra-siloxane [D4] | Decamethyl-cyclopenta-siloxane [D5] | Dodecamethyl-cyclohexa-siloxane [D6] | Tetradecamethyl-cyclohepta-siloxane [D7] | Polysiloxane of the formula II having $R^1 = R^2 = CH_3$ and a mean chain length of n = 12 |
|---|---|---|---|---|---|
| 0.0% | 0.2% | 0.3% | 0.9% | 0.5% | 98.1% |

TABLE 3

Composition of the siloxane mixture from the vapor condensate

| Content in [%] of cyclic siloxane of the general formula I having $R^1 = R^2 = CH_3$ and | | | | | | | | Content in [%] of polysiloxane of the general formula II having $R^1 = R^2 = CH_3$ and | | | | | | | | | |
|---|---|---|---|---|---|---|---|---|---|---|---|---|---|---|---|---|---|
| m = | 3 | 4 | 5 | 6 | 7 | 8 | 9 | 10 | n = | 3 | 4 | 5 | 6 | 7 | 8 | 9 | 10 | 11 | 12 |
|  | 0.1 | 11.1 | 62.3 | 12.2 | 1.0 | 0.2 | 0.0 | 0.0 |  | 0.4 | 4.6 | 4.8 | 2.0 | 0.6 | 0.2 | 0.1 | 0.0 | 0.0 | 0.0 |

Comparative Example

Not According to the Invention

The starting mixture mentioned hereinbefore is metered at a rate of 1 l/h into a laboratory short path evaporator (evaporator area ~700 cm²) at an evaporation temperature of 140° C. and a pressure of <0.5 mbar. This produces continuously approximately 70% of the amount used as sump effluent of the composition listed in table 4.

The distillate formed (approximately 30% of the amount used) is condensed separately and has the composition listed in table 5.

TABLE 4

Composition of the sump effluent

| Hexamethyl-cyclotri-siloxane [D3] | Octamethyl-cyclotetra-siloxane [D4] | Decamethyl-cyclopenta-siloxane [D5] | Dodecamethyl-cyclohexa-siloxane [D6] | Tetradeca-methylcyclo-heptasiloxane [D7] | Polysiloxane of the formula II having $R^1 = R^2 = CH_3$ and a mean chain length of n = 12 |
|---|---|---|---|---|---|
| 0.0% | 0.1% | 0.2% | 0.6% | 0.3% | 98.8% |

TABLE 5

Composition of the distillate

| Content in [%] of cyclic siloxane of the general formula I having $R^1 = R^2 = CH_3$ and | | | | | | | | Content in [%] of polysiloxane of the general formula II having $R^1 = R^2 = CH_3$ and n = | | | | | | | | | |
|---|---|---|---|---|---|---|---|---|---|---|---|---|---|---|---|---|---|
| m = | 3 | 4 | 5 | 6 | 7 | 8 | 9 | 10 | n = | 3 | 4 | 5 | 6 | 7 | 8 | 9 | 10 | 11 | 12 |
|  | 0.0 | 4.0 | 22.0 | 5.7 | 0.7 | 0.3 | 0.2 | 0.1 |  | 1.5 | 7.8 | 13.9 | 13.5 | 11.3 | 8.7 | 4.9 | 2.5 | 1.3 | 0.7 |

The invention claimed is:

1. A method for removing cyclic siloxanes from a mixture which contains cyclic siloxanes of the formula (I)

$$(R^1R^2SiO)_m \quad (I),$$

where
$R^1$ are alkyl groups having 1 to 12 carbon atoms,
$R^2$ have the meanings of $R^1$, or are aryl groups having 5 to 30 carbon atoms or alkenyl groups having 2 to 12 carbon atoms, and
m is an integer of from 3 to 20,
and which contains short-chain siloxanes having Si-bonded terminal hydroxyl groups, comprising separating the cyclic siloxanes using a steam stream at at least 650 hPa absolute, where the remaining fraction of cyclic siloxanes in the mixture, based on the sum of cyclic siloxanes of the formula (I) in which m=4 to 6, is in a range of 0-20,000 ppm by weight.

2. The method of claim 1, wherein the short-chain siloxanes having terminal Si-bonded hydroxyl groups have the formula (II)

$$HO(R^3R^4SiO)_nH \quad (II),$$

where
$R^3$ are alkyl group having 1 to 12 carbon atoms,
$R^4$ have the meanings of $R^3$, or are aryl groups having 5 to 30 carbon atoms or alkenyl groups having 2 to 12 carbon atoms, and
n is an integer from 2 to 100.

3. The method of claim 1, wherein the pressure is 800 hPa to 5000 hPa absolute.

4. The method of claim 2, wherein the pressure is 800 hPa to 5000 hPa absolute.

5. The method of claim 1, wherein the temperature is from 100° C. to 200° C.

6. The method of claim 2, wherein the temperature is from 100° C. to 200° C.

7. The method of claim 3, wherein the temperature is from 100° C. to 200° C.

8. The method of claim 4, wherein the temperature is from 100° C. to 200° C.

9. The method of claim 4, wherein the temperature of the mixture is greater than the temperature of the steam.

* * * * *